US012522793B2

(12) United States Patent
Kuang et al.

(10) Patent No.: US 12,522,793 B2
(45) Date of Patent: Jan. 13, 2026

(54) ACCURATE POSITIONING MECHANISM OF HIGH-SPEED BIOLOGICAL SHAKING TABLE

(71) Applicant: SHANGHAI ZHICHU INSTRUMENT CO., LTD., Shanghai (CN)

(72) Inventors: Yunfei Kuang, Shanghai (CN); Panpan Zhou, Shanghai (CN); Kai Cao, Shanghai (CN); Bing Qian, Shanghai (CN); Jun Qian, Shanghai (CN)

( * ) Notice: Subject to any disclaimer, the term of this patent is extended or adjusted under 35 U.S.C. 154(b) by 484 days.

(21) Appl. No.: 18/156,204

(22) Filed: Jan. 18, 2023

(65) Prior Publication Data

US 2023/0407227 A1 Dec. 21, 2023

(30) Foreign Application Priority Data

Jun. 16, 2022 (CN) ......................... 202210684090.5

(51) Int. Cl.
*B01F 31/22* (2022.01)
*C12M 1/36* (2006.01)
*C12M 3/06* (2006.01)

(52) U.S. Cl.
CPC ............. *C12M 27/16* (2013.01); *B01F 31/22* (2022.01); *C12M 41/48* (2013.01)

(58) Field of Classification Search
CPC ...... C12M 27/16; C12M 41/14; C12M 41/48; B01F 31/22; B01F 31/201; B01F 31/60; B01F 35/00; B01F 35/21; B01F 35/2202; B01F 35/60; B01F 2101/44; B01F 31/70; C09J 127/18; C09J 143/04; B01L 9/00; A21C 3/021
USPC .................................................. 366/208–209
See application file for complete search history.

(56) References Cited

U.S. PATENT DOCUMENTS

| | | | | |
|---|---|---|---|---|
| 5,558,437 | A * | 9/1996 | Rode | B01F 35/212 366/208 |
| 6,190,032 | B1 * | 2/2001 | Choda | G01M 7/045 366/208 |
| 2012/0294107 | A1 * | 11/2012 | Zamirowski | B01F 31/22 366/110 |
| 2015/0036450 | A1 * | 2/2015 | Vester | B01F 31/70 366/108 |
| 2022/0145229 | A1 * | 5/2022 | Zhang | C12M 41/14 |
| 2023/0407227 | A1 * | 12/2023 | Kuang | C12M 27/16 |

FOREIGN PATENT DOCUMENTS

DE 102016116377 A1 * 3/2018

* cited by examiner

*Primary Examiner* — Charles Cooley
(74) *Attorney, Agent, or Firm* — Clement Cheng

(57) ABSTRACT

An accurate positioning mechanism of a high-speed biological shaking table, which is characterized by comprising a servo motor, an eccentric shaft, a motor connecting disc, a positioning balancing weight, a positioning magnet and a Hall sensor, an eccentric shaft is installed at the top main body end of the servo motor, a motor connecting disc is installed on the surface of the eccentric shaft, a positioning balancing weight is arranged at the top end of the eccentric shaft, a positioning magnet is arranged on the surface of the side, away from the eccentric shaft, of the positioning balancing weight, and a Hall sensor is installed on the surface of the rocking shaft upper plate.

5 Claims, 2 Drawing Sheets

ACCURATE POSITIONING MECHANISM OF HIGH-SPEED BIOLOGICAL SHAKING TABLE

BACKGROUND OF THE INVENTION

1. Field of the Invention

The invention relates to the field of molecular biology, and more particularly, to an accurate positioning mechanism of a high-speed biological shaking table.

2. Description of the Related Art

Molecular biology is a field of science concerned with studying the structure and function of biological macromolecules at the molecular level to clarify the nature of life processes. Since the 1950s, molecular biology has been a major frontier and a basis for the development of biology. The field of molecular biology is focused especially on protein systems, protein-nucleic acid systems (centered on molecular genetics) and protein-lipid systems (i.e., biomembrane).

A high-speed biological shaking table is a laboratory equipment that is used to culture microorganisms and cells. It is similar to a regular shaking incubator but it has an additional feature that allows it to shake at high speeds. This high-speed shaking motion is used to promote the growth of the microorganisms or cells by increasing the amount of oxygen and other growth factors that are available to the culture.

The high-speed shaking can be controlled with a timer and adjustable amplitude and frequency. The temperature inside the incubator can also be controlled and typically ranges between 30-60 C. degrees, this can vary depending on the type of microorganism or cell culture used.

High-speed biological shaking tables are commonly used in microbiology, cell biology, and biotechnology research, where the growth of microorganisms or cells is critical. The high-speed shaking helps to increase the oxygenation and nutrient transfer to the culture, which can increase the growth rate and yield of the culture. It is particularly useful for the cultivation of microorganisms which require high oxygen levels to grow.

Thus, the high-speed shaking table is one laboratory equipment used in molecular biology experiments. However, in the field of existing biological shaking tables, particularly in the field of high-speed biological shaking tables, it has difficulty in achieving an accurate positioning of a shaking table motion platform. Since the high-speed biological shaking table is typically rotated at a speed of more than 1000 rpm, when operating at a high speed, the motion platform must be paused in a short period of time while ensuring that the entire motion platform finally stops at a preset position. It is a very complex process. With the gradual advancement in unmanned laboratories, biological shaking tables and robotic arms are now working collaboratively in a more frequent manner in the field of biological culture. As a result, this puts increasingly higher requirements on an accurate positioning of the biological shaking table.

SUMMARY OF THE INVENTION

An object of the present invention is to provide an accurate positioning mechanism of a high-speed biological shaking table, so that an accurate docking and fast and smooth stop of a motion platform can be achieved, and speed correction and speed control can be done in time.

In order to solve the above-mentioned problems in the prior art, the present invention provides an accurate positioning mechanism of a high-speed biological shaking table, comprising a servo motor, an eccentric shaft, a motor connecting disc, a positioning balancing weight, a positioning magnet and a Hall sensor;

wherein the eccentric shaft is installed at a top main body end of the servo motor, the motor connecting disc is installed on a surface of the eccentric shaft, the positioning balancing weight is arranged at a top end of the eccentric shaft, the positioning magnet is arranged on a surface of the side, away from the eccentric shaft, of the positioning balancing weight, and the Hall sensor is installed on a surface of the rocking shaft upper plate.

Furthermore, two rocking shaft plates installed on the surface of the main body of the servo motor are fixedly connected by a support column.

Furthermore, the main body of the servo motor forms a transmission structure through the eccentric shaft and the motor connecting disc.

Furthermore, the positioning balancing weight forms a drive in an inner wall of the motor connecting disc through the eccentric shaft.

Furthermore, a signal passing hole is arranged at a surface of the motor connecting disc, and the signal passing hole is sized to be in conformity with the positioning magnet.

Furthermore, the Hall sensor is fixed on the surface of the rocking shaft upper plate though thread snaps on the surface of the rocking shaft upper plate.

Compared with the prior art, the present invention has the following beneficial effects.

A positioning balancing weight and a Hall sensor are added on the whole movement mechanism. The centripetal force generated by the eccentric shaft can be balanced through the installation of the balancing weight, so that the whole driving mechanism achieves dynamic balance, and the stability of the machine is improved. In addition, a positioning magnet is installed on the positioning balancing weight, after the motor rotates by 360 degrees, the magnet's signal can be captured by the Hall sensor through a signal passing hole, then the signal is transmitted to a control system. Through this feedback system, position information of the platform can be fed back to the control system in the form of signals at any time, so as to realize an accurate positioning of a biological shaking table platform. Through the feedback system, the actual speed can also be compared with a preset speed, so as to correct a deviation between the actual speed and the preset speed, so that the speed can be precisely controlled during operation.

Figure 1:
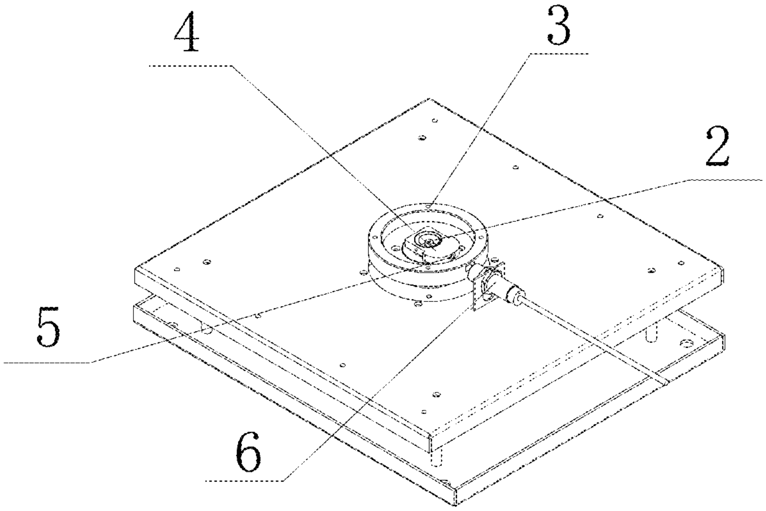
FIG. 1 is a schematic diagram of an overall three-dimensional structure of an accurate positioning mechanism of a high-speed biological shaking table according to the present invention.

The following call out list of elements can be a useful guide for referencing the element numbers of the drawings.

1 servo motor output end
2 eccentric shaft
3 motor connecting disc
4 balancing weight
5 positioning magnet
6 Hall sensor
101 main body
103 rocking shaft upper plate
102 rocking shaft lower plate
5 Hall sensor
603 thread snaps
3 rocking shaft upper plate

DETAILED DESCRIPTION

An accurate positioning mechanism of a high-speed biological shaking table provided in the present invention will be described more fully hereinafter with reference to the accompanying drawings, in which preferred embodiments of the invention are shown. It will be understood that those skilled in the art can modify the present invention while achieving beneficial effects. Thus, the following descriptions shall be construed to be well understood by those skilled in the art, and should not be construed as a limitation for the present invention.

The present invention will be illustrated by way of examples in the following paragraphs with reference to the accompanying drawings. Advantages and features of the present invention will become apparent from the following detailed description and the appended claims. It should be noted that the drawings are only schematic, and the size of the drawings are not drawn to scale. They are only drawn to explain objects of the embodiments of the present invention in a convenient and clear manner.

Figure 2:
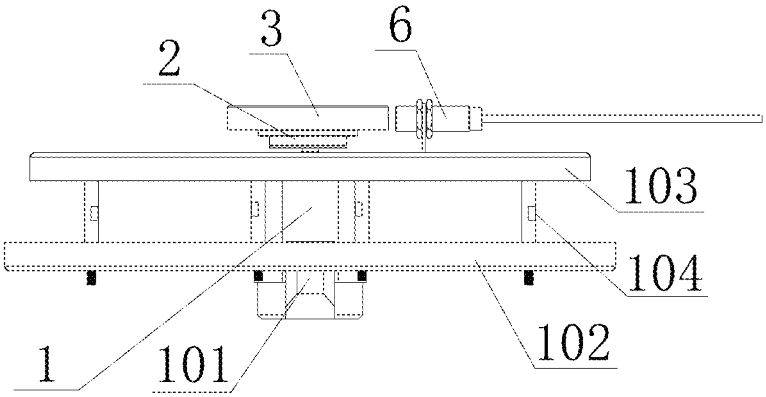
FIG. 2 is a schematic diagram of a side sectional view of an accurate positioning mechanism of a high-speed biological shaking table according to the present invention.

As shown in FIGS. 1 and 2, in an embodiment, the present invention provides an accurate positioning mechanism of a high-speed biological shaking table, comprising a servo motor 1, an eccentric shaft 2, a motor connecting disc 3, a positioning balancing weight 4, a positioning magnet 5 and a Hall sensor 6;

wherein the eccentric shaft 2 is installed at a top main body 101 end of the servo motor, the motor connecting disc 3 is installed on a surface of the eccentric shaft 2, the positioning balancing weight 4 is arranged at a top end of the eccentric shaft 2, the positioning magnet 5 is arranged on a surface of the side, away from the eccentric shaft 2, of the positioning balancing weight 4, and the Hall sensor 6 is installed on a surface of the rocking shaft upper plate 103.

In this embodiment, as shown in FIG. 1, the main body 101 of the servo motor is started during the operation, the main body 101 of the servo motor drives the eccentric shaft 2 to rotate, and then drives the motor connecting disc 3 on the surface of the eccentric shaft 2 to work. The amplitude produced by the eccentric shaft 2 is transmitted to a motion platform of the biological shaking table through the motor connecting disc 3. In the meantime, the point balancing weight 4 arranged on the eccentric shaft 2 is driven by the main body 101 of the servo motor and rotates in an inner wall of the motor connecting disc 3. Then the centripetal force generated during the operation of the motor connecting disc 3 can be balanced, so that the whole driving mechanism achieves dynamic balance when it is working, and the stability of the shaking table is improved during its operation. In addition, the positioning magnet 5 is arranged on a surface of the side of the positioning balancing weight 4. After the positioning balancing weight 4 rotates by 360 degrees inside the motor connecting disc 3, the positioning magnet 5's signal is captured by the Hall sensor 6 installed on a surface of the rocking shaft upper plate 103 through a signal passing hole on the surface of the motor connecting disc 3, then the signal is transmitted to a control system. Through this feedback system, position information of the platform can be fed back to the control system in the form of signals at any time, so as to realize an accurate positioning of a biological shaking table platform. Through the feedback system, the actual speed can also be compared with a preset speed, so as to correct a deviation between the actual speed and the preset speed, so that the speed can be precisely controlled during operation.

Two rocking shaft plates installed on the surface of the main body 101 of the servo motor are fixedly connected by a support column 104. In this embodiment, the rocking shaft upper plate 103 and a rocking shaft lower plate 102 are fixedly connected by the support column 104, and the servo motor is fixed between the rocking shaft upper plate 103 and a rocking shaft lower plate 102, so that instability of the main body 101 of the servo motor resulting from the amplitude of the motor connecting disc 3 and the motion platform can be avoided during its operation.

The main body 101 of the servo motor forms a transmission structure through the eccentric shaft 2 and the motor connecting disc 3. In this embodiment, the servo motor main body 101 drives the eccentric shaft 2 to rotate when it is running, and the motor connecting disc 3 generates amplitude movement under the action of the eccentric shaft 2, and then the motor connecting disc 3 transmits the amplitude to the motion platform for operation.

Figure 3:
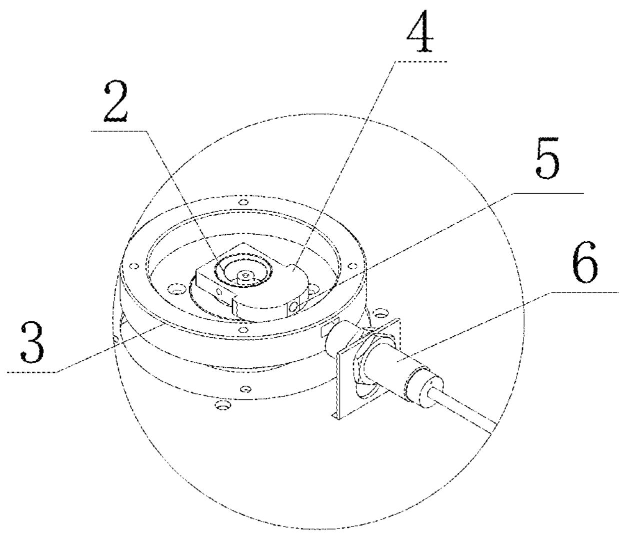
FIG. 3 is a schematic diagram of an overall structure of a driving structure of an accurate positioning mechanism of a high-speed biological shaking table according to the present invention.
Figure 4:
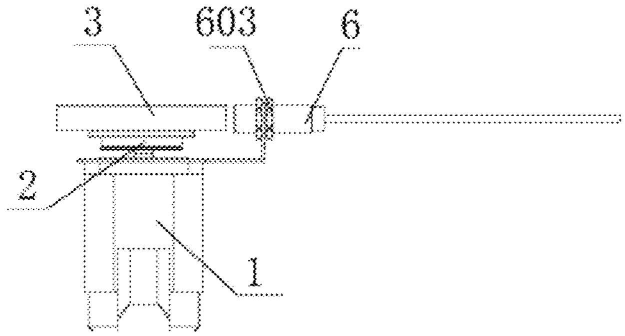
FIG. 4 is a schematic diagram of an overall structure of a Hall sensor of an accurate positioning mechanism of a high-speed biological shaking table according to the present invention.

The positioning balancing weight 4 forms a drive in an inner wall of the motor connecting disc 3 through the eccentric shaft 2, as shown in FIG. 3. In this embodiment, a signal passing hole is arranged at a surface of the motor connecting disc 3, and the signal passing hole is sized to be in conformity with the positioning magnet 5. Since a positioning balancing weight 4 and a Hall sensor 6 are added on the movement mechanism; the centripetal force generated by the eccentric shaft 2 can be balanced through the installation of the positioning balancing weight 4, so that the whole driving mechanism achieves dynamic balance, and the stability of the machine is improved. In addition, a positioning magnet 5 is installed on the positioning balancing weight 4, after the main body of the servo motor 1 rotates by 360 degrees, the positioning magnet 5's signal can be captured by the Hall sensor 6 through the signal passing hole.

The Hall sensor 6 is fixed on the surface of the rocking shaft upper plate 103 though thread snaps 603 on the surface of the rocking shaft upper plate 103. In this embodiment, the positioning magnet 5's signal can be transmitted to a control system by the Hall sensor 6. Position information of the platform can be fed back to the control system in the form of signals at any time, so as to realize an accurate positioning of a biological shaking table platform. Through the feedback system, the actual speed can also be compared with a preset speed, so as to correct a deviation between the actual speed and the preset speed, so that the speed can be precisely controlled during operation.

It will be apparent that many modifications and variations can be made by those skilled in the art without departing from the scope and spirit of the invention. In this way, if those modifications and variations fall within the scope of the claims and equivalents of the invention, the invention is construed to be included in those modifications and variations.

What is claimed is:

1. An accurate positioning mechanism of a biological shaking table, comprising a servo motor, an eccentric shaft, a motor connecting disc, a positioning balancing weight, a positioning magnet and a Hall sensor:

wherein the eccentric shaft is installed at a top end of a main body of the servo motor, the motor connecting disc is installed on a surface of the eccentric shaft, the positioning balancing weight is arranged at a top end of the eccentric shaft, the positioning magnet is arranged on a surface of a side, away from the eccentric shaft, of the positioning balancing weight, wherein two rocking shaft plates installed on the surface of the main body of the servo motor are fixedly connected by a support column; and the Hall sensor is installed on a surface of one of the two rocking shaft plates.

2. The accurate positioning mechanism of a biological shaking table of claim 1, wherein the main body of the servo motor forms a transmission structure through the eccentric shaft and the motor connecting disc.

3. The accurate positioning mechanism of a biological shaking table of claim 1, wherein the positioning balancing weight forms a drive in an inner wall of the motor connecting disc through the eccentric shaft.

4. The accurate positioning mechanism of a biological shaking table of claim 1, wherein a signal passing hole is arranged at a surface of the motor connecting disc, and the signal passing hole is sized to be in conformity with the positioning magnet.

5. The accurate positioning mechanism of biological shaking table of claim 1, wherein the Hall sensor is fixed on the surface of one of the two rocking shaft plates though thread snaps on the surface of one of the two rocking shaft plates.

* * * * *